Sept. 24, 1974 MARIE-LOUISE MEILLAND Plant Pat. 3,621
ROSE PLANT
Filed July 2, 1973
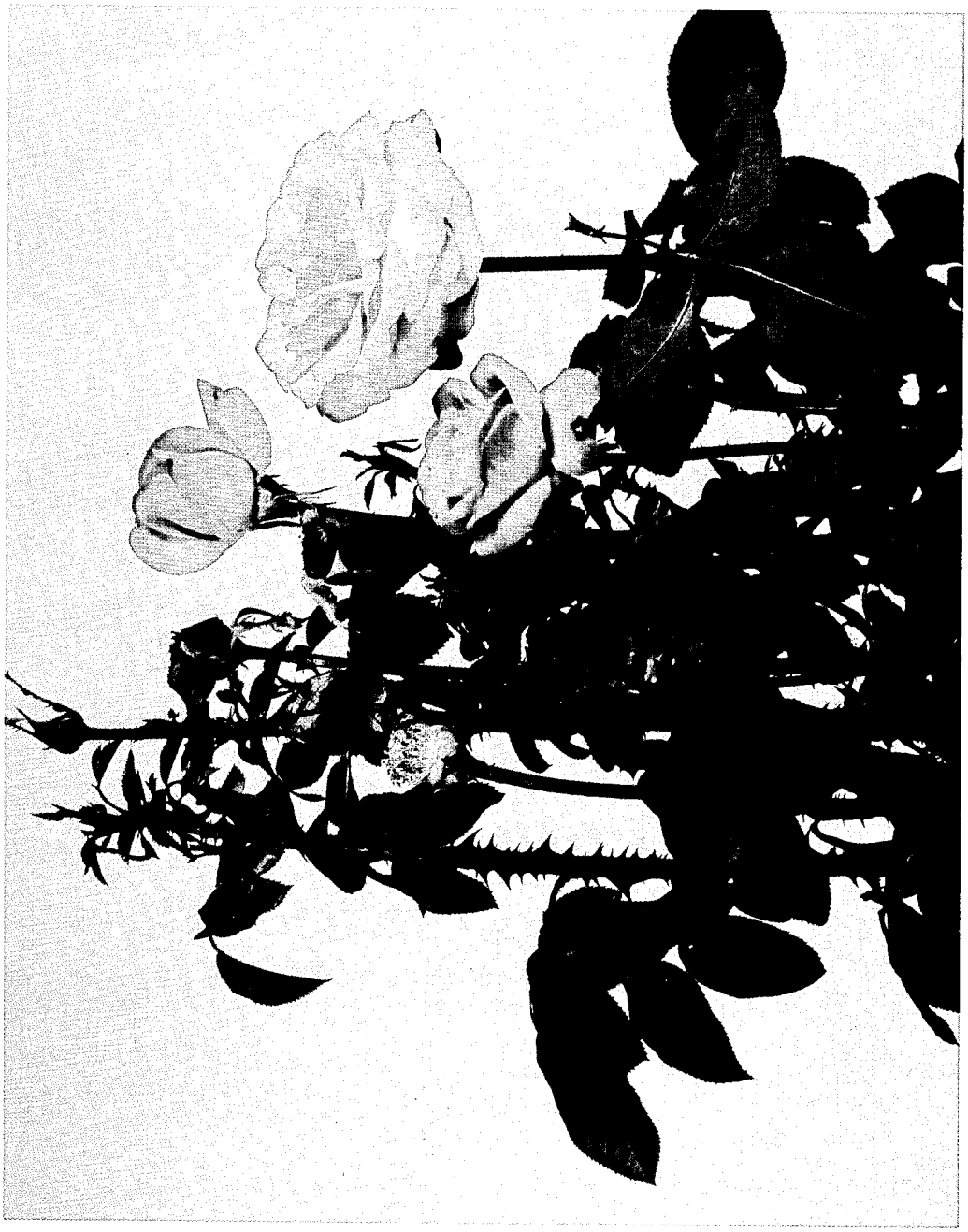

United States Patent Office

Plant Pat. 3,621
Patented Sept. 24, 1974

3,621
ROSE PLANT

Marie-Louise Meilland, Antibes, France, assignor to Michigan Bulb Company, Grand Rapids, Mich.

Filed July 2, 1973, Ser. No. 375,442
Int. Cl. A01h 5/00
U.S. Cl. Plt.—20 1 Claim

ABSTRACT OF THE DISCLOSURE

A rose plant of the Hybrid Tea class produced by crossing an unnamed seedling produced by crossing Royal Velvet (U.S. Plant Pat. No. 1,911) with Chrysler Imperial (U.S. Plant Pat. No. 1,167), which unnamed seedling was crossed with Pharoah (U.S. Plant Pat. No. 2,859).

SUMMARY OF THE INVENTION

The present invention relates to a new and distinct variety of rose plant of the Hybrid Tea class, which was originated by me by crossing an unnamed seedling by crossing Royal Velvet (U.S. Plant Pat. No. 1,911) with Chrysler Imperial (U.S. Plant Pat. No. 1,167), which unnamed seedling was crossed with Pharaoh (U.S. Plant Pat. No. 2,859).

As a result of this breeding, I have produced a new, improved and useful rose variety which is distinguished from its parents and all other roses of which I am aware, as evidenced by the following unique combination of characteristics which are outstanding therein:

1. Intense, vivid orange-red color.
2. Well formed, attractive bud of distinctive color.
3. Attractive, large flower of good form and vivid color which becomes more intense in cool weather.
4. Upright plant of well branched growth habit carrying flowers usually one to the stem at the top of the plant.
5. Dark, glossy green foilage of large size covering the plant well.
6. An abundance of prickles large, medium and small on all stems and branches.

The seed parent of my new discovery was an unnamed seedling of a cross of Royal Velvet (U.S. Plant Pat. No. 1,911) with Chrysler Imperial (U.S. Plant Pat. No. 1,167), characterized by bright red color and compact, well branched plant. My new discovery differs from its seed parent by having an open flower of more flat form with petals only lightly roller outward, with more orange tones in the flower color and a plant which grows taller and with more glossy foliage.

As compared with its pollen parent, Pharaoh (U.S. Plant Pat. No. 2,859), my new rose has more orange color in the flower with less black-red marking on the outer petal and a plant of more upright and taller growth producing more flowers on shorter stems.

Asexual reproduction of my new rose by budding as performed in France and at West Grove, Pa., shows that the distinguishing characteristics come true to form and are established and transmitted through succeeding propagations.

BRIEF DESCRIPTION OF DRAWING

The accompanying drawing shows typical specimens of the vegetative growth and flowers of my new rose in different stages of development and as depicted in color as nearly true as it is reasonably possible to make the same in a color illustration of this character.

DETAILED DESCRIPTION OF DISCLOSURE

The following is a detailed description of the new variety, with color terminology in accordance with the Colour Chart of the Royal Horticultural Society, except where general color terms of ordinary dictionary significance are obvious:

Type: Hardy; tall bush outdoor; seedling; garden decoration.
Class: Hybrid Tea.
Propagation: It does hold its distinguishing characteristics through succeeding propagations by budding.

FLOWER

Locality where grown: West Grove, Pa.
Flowers Borne: Singly, several to stem; in irregular cluster; strong; medium long stems.
Quantity of bloom: Free outdoors.
Continuity: Continuous.
Fragrance: Slight; tea.
Bud: Peduncle: Medium long; medium heavy; erect, light reddish (general color term); almost smooth; few hairs; red (general color term).
*Before calyx breaks*: Size: Small. Form: Short, ovoid; with foliaceous appendages on the surface of the bud; with medium width, medium cut foliaceous parts extending beyond the tip of the bud equal to ¼ to ½ or more of its length.
*As calyx breaks*: Color: 46A.
*As first petal opens*: Size: Medium. Form: Medium ovoid. Color: Outside: 45A; inside: 40A. Opening: It does open up well.
Bloom: *Size when fully open*: Medium large, 3½ to 4½ inches.
*Petalage*: Double; from 25 to 35 petals; arranged regularly.
*Form*: Cupped at first; becoming flat; petals remaining at first tightly cupper rolled inward; becoming later at maturity loosely flat rolled outward.
Petals: Leathery; with inside velvety; outside satiny.
*Shape*: Outer: Obovate; with 1 notch. Intermediate: Round; scalloped with apex flat; with 1 tooth. Inner: Round; with apex flat.

This description of a newly opened flower was made from a rose grown in early September 1971, at West Grove, Pa.

*Color*: Outer petal: Outside surface: 50A, some petals on some flowers have a white center stripe part way or all the way up the center of the petal. (This is true in all stages of development.) Inside surface: 43A, some petals of some flowers have a white center stripe part way or all the way up the center of the petal. (This is true in all stages of development.) Intermediate petal: Outside surface: 50A; inside surface: 43A. Inner petal: Outside surface: 50A; inside surface: 43A.

This description was made from a rose that was open for three days outdoors in early September 1971, at West Grove, Pa.

*Color*: Outer petal: Outside surface: 51A; inside surface: 50A. Inner petal: Outside surface: 51A; inside surface: 50A.
General color effect:
*Newly opened flower*: 43A.
*Three days open*: 50A.
Behavior: Drop off cleanly; affected by cool weather—more intense colors.
Flower longevity: On bush in garden 3 days in early September, cut roses grown outdoors kept at living room temperatures 3 days in early September.

REPRODUCTIVE ORGANS

Stamens: Many; arranged regularly about pistils.
Filaments: Many, most with anthers; medium long.
*Color*: 43C.

Anthers: All open at once; medium large.
*Color*: 19A.
Occasionally an anther fused with a petaloid.
Pollen: Moderate; yellow.
Pistils: Many.
Styles: Uneven; short; thin; bunched columnar.
Stigma: Yellow.
Ovaries: Some protruding from receptacle.
Hips: Very short, globular with inconspicuous neck; smooth; medium fleshy; green.
Sepals: Falling soon to permanent; long; spear shaped.
Seeds: Medium amount; medium size.

PLANT

Foliage:
*Leaves*: Compound of 3, 5 leaflets; normal amount, medium large; leathery.
*Leaflets*: Shape: Ovoid with apex acute, base acute, simply serrate.
*Color*: Mature—Upper surface: 147A; under surface: 147B. Young—Upper surface: 136A; under surface: 136 B.
*Rachis*: Medium heavy. Upper side: Smooth; grooved. Under side: Sparsely thorny.
*Stipules*: Medium length; medium width; moderately short points; turning out at an angle of more than 45°.
*Disease*: Resistance comparable to the average variety growing under the same cultural conditions.

Growth:
*Habit*: Upright, much branched.
*Growth*: Vigorous.
*Canes*: Medium heavy.
*Main stems*: Dull. Color: 14B. Prickles: Many. Color: Most 165A, some 161A. Hairs: None.
*Branches*: Dull. Color: 146B. Prickles: Several. Color: Most 165A, some 161A. Hairs: None.
*New Shoots*: Bright. Color: One side 178A, other side 146A. Prickles: Many. Color: 178A. Hairs: None.

I claim:

1. A new and distinct variety of rose plant of the Hybrid Tea class, substantially as herein shown and described, characterized particularly as to novelty by the unique combination of a tall, vigorous, upright, freely branched habit of growth; with all canes and branches attractively covered with large, glossy, dark green foliage, and with the presence of a large number of prickles, flowers of vivid and intense orange-red color, large size with bud of attractive form and open flower of flat form with petals lightly rolled outward often showing the stamens and having a light tea fragrance, the plant having winter hardiness and resistance to disease typical of the Hybrid Tea class.

No references cited.

ROBERT E. BAGWILL, Primary Examiner